United States Patent [19]

Mohr et al.

[11] Patent Number: 4,867,212
[45] Date of Patent: Sep. 19, 1989

[54] SAFETY ARRANGEMENT FOR FILLING AND EMPTYING AN ANESTHETIC VAPORIZER

[75] Inventors: Helmut Mohr, Stockelsdorf; Wolfgang Falb, Klein Wesenberg; Carl-Friedrich Wallroth, Lübeck, all of Fed. Rep. of Germany

[73] Assignee: Drägerwerk Aktiengesellschaft, Lübeck, Fed. Rep. of Germany

[21] Appl. No.: 204,860

[22] Filed: Jun. 10, 1988

[30] Foreign Application Priority Data

Jun. 19, 1987 [DE] Fed. Rep. of Germany ....... 3720326

[51] Int. Cl.⁴ .............................................. B65B 3/06
[52] U.S. Cl. .................................. 141/290; 141/301; 141/302; 141/319; 128/203.12; 128/200.14
[58] Field of Search .............. 141/319, 321, 382, 383, 141/384, 385, 386, 387, 388, 389, 301, 302, 303, 304, 305, 290, 44, 45, 46, 59; 137/588, 212; 222/481, 481.5, 522, 523, 513, 484

[56] References Cited

U.S. PATENT DOCUMENTS

| | | | |
|---|---|---|---|
| 1,165,711 | 12/1915 | Ransom, Jr. | 222/484 |
| 2,154,647 | 4/1939 | West | 141/382 |
| 2,308,181 | 1/1943 | Laird | 141/305 |
| 3,263,711 | 8/1966 | Laub | 141/59 |
| 3,530,905 | 9/1970 | Dräger et al. | 141/18 |
| 3,540,402 | 11/1970 | Kocher | 222/484 |
| 3,578,042 | 5/1971 | Breiling | 141/301 |
| 3,590,890 | 7/1971 | Young | 141/382 |
| 4,210,975 | 7/1980 | Teague, Jr. et al. | 285/134 |
| 4,254,972 | 3/1981 | Wiedenbeck et al. | 285/134 |
| 4,260,183 | 4/1981 | Krupp | 285/134 |
| 4,676,241 | 6/1987 | Webb et al. | 128/912 |
| 4,722,463 | 2/1988 | Anderson | 137/588 |
| 4,759,475 | 7/1988 | Munthe | 222/518 |
| 4,760,865 | 8/1988 | Rilett | 131/588 |

FOREIGN PATENT DOCUMENTS 2189472 10/1987 United Kingdom ........... 128/203.12

OTHER PUBLICATIONS

DE3500895A1, German Offenkgungsschrift, 7/17/86, FIGS. 1 and 2.
Safety Filling System for Vapor 19.1 (No. 5437.09), Dec. 19, 1984.

Primary Examiner—Henry J. Recla
Assistant Examiner—Edward C. Donovan
Attorney, Agent, or Firm—Walter Ottesen

[57] ABSTRACT

A safety arrangement for filling and emptying an anesthetic vaporizer via a supply vessel connected thereto includes a movable tube-shaped conducting member having first and second ends. A vessel-connecting piece is provided on its first end and an index member is provided on its second end for engaging a vaporizer. The tubular-shaped conducting member has a ventilating channel separate from the filling channel and the safety arrangement is improved with respect to its use characteristics. This improvement is obtained in that a joint piece is connected to the second end of the tubular conducting member intended for the vaporizer. An index member is rotatably journalled in the joint piece and contains respective line segments of the filling channel and the ventilating channel.

9 Claims, 2 Drawing Sheets

SAFETY ARRANGEMENT FOR FILLING AND EMPTYING AN ANESTHETIC VAPORIZER

FIELD OF THE INVENTION

The invention relates to a safety arrangement for filling and emptying an anesthetic vaporizer via a connected supply vessel. The safety arrangement includes a movable tubular conducting member which includes a vessel connecting piece at its first end and is provided with an index member on its second end for engaging with the vaporizer. The tubular conducting piece has a ventilating channel separated from the filling channel.

BACKGROUND OF THE INVENTION

The application of a safety filling system is prescribed for filling an anesthetic vaporizer. In this safety filling system, the filling tube has a non-interchangeable index member for engaging the vaporizer and has a coded vessel cap for making an exclusive connection with a supply vessel having a predetermined filling. The tubular conducting member must be lifted for the filling operation when the anesthetic vessel is connected thereto and must again be lowered for emptying.

The publication of Drgerwerk Aktiengesellschaft entitled "Safety Filling System for Vapor 19.1" (No. 5327.09) of Dec. 19, 1984 discloses the application of a tubular conducting member in the form of an elastic filling hose. In this application, bending loads occur which can lead to a premature wear and a fatigue fracture at the connecting location which is dangerous during use. Furthermore, it is difficult to close off the filling hose during non-use so that a run-out of the anesthetic liquid and of the vapors is reliably prevented. A further difficulty associated with the use of such filling hoses is that elastic plastic materials must contain srfteners which can be dissolved out by the anesthetic and reach the breathing air loop of the patient in an impermissible manner.

U.S. Pat. No. 3,530,905 discloses a vaporizer for an anesthetic having a pivotable connecting piece for attaching a supply vessel. This connecting piece includes a coded bottle-connecting stub adapted only for bottles that fit and contains a valve which is open when a bottle containing the anesthetic is utilized or when a flexible connecting piece is introduced. Such an arrangement requires improvement with reference to handling.

SUMMARY OF THE INVENTION

It is an object of the invention to provide a safety arrangement of the kind described above which includes a tubular conducting member and a joint member connected to the conducting member at the vaporizer end of the latter. A blockable index member is rotatably journalled in the joint piece and the index member contains conduit segments of the filling channel and the ventilating channel. Because of the rotatable joint formed between the joint piece and the index member, it is not necessary to apply a bending load to the tubular conducting member for lifting and lowering during the filling or emptying operation. Furthermore, it is possible to utilize rigid metal or inflexible plastic materials free of softeners. With the application of form-rigid materials, constant cross sections of the filling channel and of the ventilating channel are obtained and uniform filling and emptying times are achieved for various safety arrangements of the same kind independent of batch.

A blocking device can be advantageously integrated in the region of the rotatable joint formed between the index member and the joint piece. The blocking device is switchable between a blocking position and a release position and in the blocking position, this device closes off the filling channel and the ventilating channel. The blocking device is preferably configured so as to be movable in such a manner that it moves into the blocking position when the index member is removed from the vaporizer. The blocking device can be actuated by means of an axial displacement as well as also by means of a radial rotation of the index member. However, a hand-actuated valve appears to be advantageous for specific applicational purposes.

According to a preferred embodiment of the invention, the index member can be displaceably journalled in the joint piece in the manner of a piston against a pressure spring and have conduit segments which are independent of rotational position and which communicate with the filling channel as well as with the ventilating channel only in the release position. The ventilating channel can be advantageously configured as a central conduit piece which engages at one end in the index member and in a piston-like guide part with the index member and the piston-like guide part being rotatably or displaceably and rotatably journalled as a component in the joint piece. The conduit connection is independent of rotational position and is preferably configured as slots formed on the periphery of the index member and/or on the guide part.

The tubular conducting member is advantageously assembled from an outer filling tube made of metal or transparent or translucent plastic free of softeners and an inner ventilating tube made of metal or another material which is resistant to anesthetic. The index member and the joint piece are nickel-plated brass parts or can be made of corrosion-free materials resistant to anesthetic. Alternatively, these parts can be made of softener-free plastic such as polyamide. The sealing elements for providing a seal between the joint piece and the index member rotatably journalled therein are advantageously O-ring seals resistant to anesthetic and can be made, for example, from fluorinated rubber.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
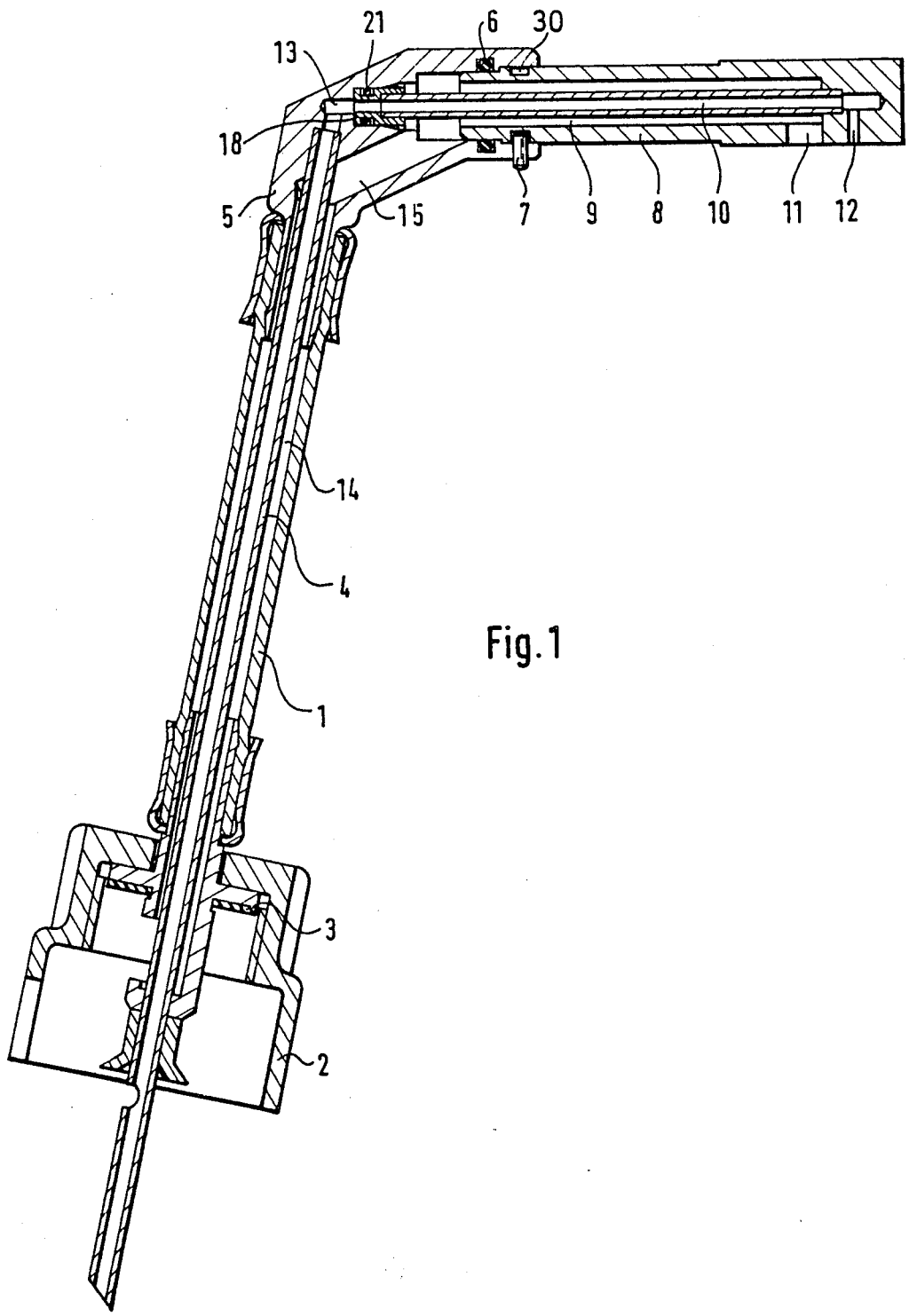
FIG. 1 is a longitudinal section taken through a safety arrangement according to a first embodiment of the invention.

FIG. 1 shows a tubular conducting member 1 having first and second ends with a vessel connector configured as a threaded cap 2 provided at the first end. A seal disk 3 is provided in the threaded cap for sealing a bottle containing anesthetic which is not shown and which threadably engages the threaded cap.

The tubular conducting member 1 is made of a softener-free transparent or translucent plastic or of metal and has an interior space for accommodating a metal ventilating tube 4. A joint piece 5 is connected to the second end of the tubular conducting member 1.

An index member 8 is disposed in the joint piece 5 and is sealed at its periphery with an O-ring seal 6. The index member 8 accommodates line segment 9 of the filling channel and a centrally disposed line segment 10 of the ventilating channel. The outlet openings (11, 12) of the filling channel and ventilating channel of the line segments (9, 10), respectively, can be closed by a sealing cap for blocking. The sealing cap is removable when the system is in use and is placed on the index member 8.

A pin 7 is located in the joint piece 5 and engages an annular slot 30 of the index member 8 and secures the index member 8 against axial displacement in the joint piece 5.

The line segment 10 of the ventilating channel is connected via a connecting bore passage 13 with the ventilating tube 4 with a hollow guide part 18 connected therebetween. The guide part 18 is rotatable with the index member 8 and has an O-ring seal 21 as shown.

The filling channel 14 is formed in the tubular conducting member 1 and is connected with the line segment 9 of the filling channel via a connecting passage 15 disposed in the joint piece 5.

When a vessel containing anesthetic is attached to the threaded cap 2, the index member 8 is guided into the corresponding receiving opening on the anesthetic vaporizer. The filling or emptying operation can be carried out by pivoting the tubular part 1 with the vessel containing anesthetic attached thereto about the rotational joint with the latter being formed in the joint piece 5 so as to permit rotation with respect to the index member 8.

Figure 2:
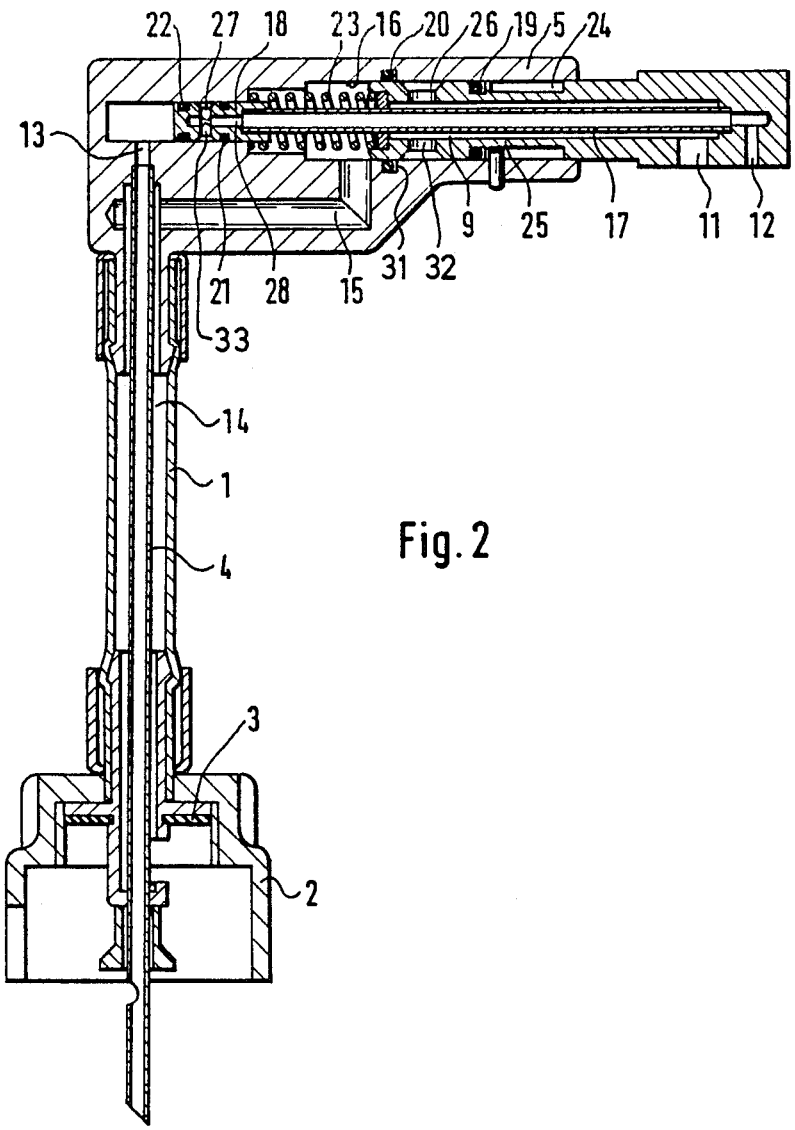
FIG. 2 is a longitudinal section taken through an alternate embodiment of the safety arrangement according to the invention which is equipped with a blocking device shown in its blocking position; and, FIG. 3 is a portion of the safety arrangement of FIG. 2 showing the blocking device in its release position.
Figure 3:
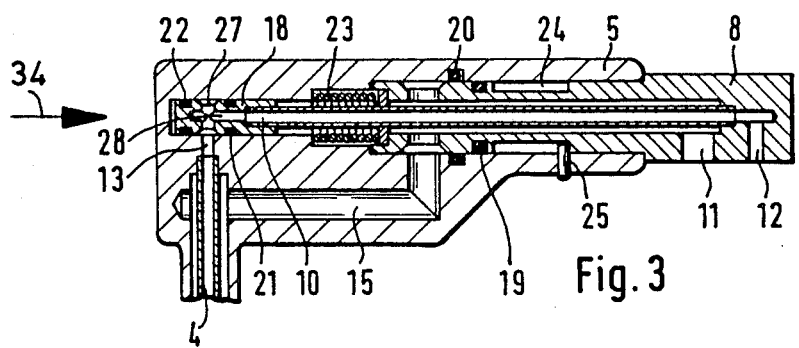

In the embodiment according to FIGS. 2 and 3, a blocking device is integrated in the region of the rotational joint formed between the index member 8 and the joint piece 5. The blocking device closes off the filling channel and the ventilating channel in its blocking position.

FIG. 2 shows the safety filling system in its blocking condition.

In the embodiment of FIG. 2, the index member 8 is displaceable in a piston-like manner in a bore 16 of the joint piece 5 and is connected via a central conduit section 17 of the ventilating channel with a guide part 18 which is likewise configured so as to have a piston-like configuration. O-ring seal 19 is provided on index member 8 and is displaceable therewith. Likewise, O-ring seals (21, 22) are provided on the piston-like guide part 18 and are likewise displaceable therewith. A further stationary O-ring seal 20 is provided in a slot 31 of the bore 16.

The index member 8 lies against a helical pressure spring 23 braced in the joint piece 5 and is thereby urged into the blocking position shown in FIG. 2 in which the line segments (9, 10) of the filling channel and the ventilating channel, respectively, are blocked with respect to corresponding parts in the tubular conducting member 1. The displacement of the index part 8 in the joint piece 5 is limited by an indexing part 25 engaging into a hollow cylindrically-shaped annular recess 24.

The line segment 9 of the filling channel communicates with a peripheral annular beveled slot 26 via bore 32 so as to be independent of position. The line segment 10 of the ventilating channel communicates with a beveled slot 27 via bore 33 of the guide part 18. The slot 27 is formed in the periphery of the guide part 18 and is formed in a manner similar to annular slot 26.

FIG. 3 shows the operating position wherein the index member 8 is guided into the vaporizer while at the same time pressure is applied to the joint piece 5 in the direction of the arrow 34. In this way, the index member 8 is displaced in the joint piece 5 and takes along the guide part 18 into the position shown. In this position, the through paths of the filling channel and of the ventilating channel are cleared and communicate with the stationary line passage 15 and the connecting bore passage 13, respectively.

The parts shown in FIGS. 2 and 3 which are not referred to correspond to the same components shown in FIG. 1.

It is understood that the foregoing description is that of the preferred embodiments of the invention and that various changes and modifications may be made thereto without departing from the spirit and scope of the invention as defined in the appended claims.

What is claimed is:

1. Safety arrangement for filling and emptying an anesthetic vaporizer having an inlet means for supplying anesthetic medium and relieving gas to and from said vaporizer, said anesthetic medium contained within a supply vessel, the safety arrangement comprising:

a movable tubular conducting member having first and second ends and including structure defining a first ventilating channel segment and a first filling channel segment separated from said ventilating channel segment;

vessel connecting means provided on said first end for detachably connecting the supply vessel to said tubular conducting member;

a joint member having two end portions defining respective axes conjointly defining an angle therebetween less than 180° and one of said end portions being connected to said second end of said tubular conducting member;

an index member adapted to be inserted into said inlet means for communicating with the vaporizer and defining a longitudinal axis, said index member including means for preventing said index member from rotating with respect to the vaporizer when inserted into said inlet means and having structure defining a second ventilating channel segment and a second filling channel segment;

journalling means formed in the other one of said end portions of said joint member for rotatably journalling said joint member on said index member so as to permit said joint member and said conducting member to conjointly rotate about said longitudinal axis to swing the supply vessel from a location beneath said longitudinal axis to a location above said longitudinal axis thereby causing the contents of the vessel to flow from the latter and down through said first filling channel and then through said filling passage means to said second filling channel; and, said joint member including ventilating passage means for interconnecting said first and second ventilating channel segments and filling passage means for interconnecting said first and second filling channel segments irrespective of the angular position of said index member relative to said joint member.

2. The safety arrangement of claim 1, said index member being displaceably mounted in said joint member; and, the arrangement further comprising blocking means for blocking and clearing said ventilating passage means and said filling passage means in dependence upon the position of said index member in said joint member.

3. The safety arrangement of claim 2, said index member being movably mounted in said joint member from a first position wherein the vaporizer is disconnected from said index member and said blocking means blocks said passages to a second position wherein said vaporizer is connected to said index member and said blocking means clears said passages.

4. The safety arrangement of claim 3, said index member defining a longitudinal axis and said index member being displaceably mounted in said joint member so as to be displaceable along said axis between said first and second positions.

5. The safety arrangement of claim 4, said joint member having an elongated cylindrical opening for accommodating said index member therein; said arrangement further comprising a pressure spring arranged in said cylindrical opening so as to be interposed between said joint member and said index member; said index member being disposed in said cylindrical opening in the manner of a piston so as to be displaceable between said positions against the force of said spring; said index member including first and second ancillary passages formed therein for interconnecting corresponding ones of said ventilating and filling passage means with said second ventilating channel and said second filling channel, respectively, when said index member is in said second position.

6. The safety arrangement of claim 5, said structure of said index member including a conduit section defining said second ventilating channel segment and being coincident with said longitudinal axis; said arrangement further including a piston-like guide part displaceably mounted in said joint member so as to be movable along said axis; and, said conduit section having first and second end portions connected with said guide part and said index member, respectively, so as to cause said guide part to be movable with said index member; said index member having a cylindrical cavity formed therein along said axis for accommodating said conduit section, said conduit section and the wall surface of said cavity conjointly forming an annular space defining said second filling channel segment.

7. The safety arrangement of claim 6, said first ancillary passage being formed in said guide par for interconnecting said conduit section and said ventilating passage means independently of the angular position of said index member relative to said joint member when said index member is in said second position; and, said second ancillary passage being formed in said index member for interconnecting said annular space and said filling passage means also independently of the angular position of said index member relative to said joint member when said index member is in said second position.

8. The safety arrangement of claim 6, further comprising first anesthetic resistant O-ring seal means interposed between said index member and the wall surface of said cylindrical opening; and, second anesthetic resistant O-ring seal means interposed between said guide part and joint member.

9. The safety arrangement of claim 1, said structure of said tubular conducting member including an outer filling tube made of softener-free transparent plastic and an inner ventilating tube made of metal defining said first ventilating channel segment; and, said outer filling tube and said inner ventilating tube conjointly forming an annular space defining said first filling channel segment.

* * * * *

UNITED STATES PATENT AND TRADEMARK OFFICE
CERTIFICATE OF CORRECTION

PATENT NO. : 4,867,212

DATED : September 19, 1989

INVENTOR(S) : Helmut Mohr, Wolfgang Falb and Carl-Friedrich Wallroth

It is certified that error appears in the above-identified patent and that said Letters Patent is hereby corrected as shown below:

On the title page, under "OTHER PUBLICATIONS": delete "Offenkgungsschrift," and substitute -- Offenlegungsschrift, -- therefor.

On the title page, under "OTHER PUBLICATIONS": delete "(No. 5437.09)," and substitute -- (No. 5327.09), -- therefor.

In column 1, line 26: delete "Drgerwerk" and substitute -- Drägerwerk -- therefor.

In column 1, line 37: delete "srfteners" and substitute -- softeners -- therefor.

In column 6, line 14: delete "par" and substitute -- part -- therefor.

Signed and Sealed this

Twenty-first Day of August, 1990

Attest:

HARRY F. MANBECK, JR.

Attesting Officer

Commissioner of Patents and Trademarks